United States Patent [19]
Frenkel et al.

[11] Patent Number: 6,054,625
[45] Date of Patent: Apr. 25, 2000

[54] HETEROPOLYACIDS AS CATALYSTS FOR A SYNTHESIS OF KETONE PEROXIDES

[75] Inventors: Peter Frenkel; Delphine Nwoko; Ted M. Pettijohn, all of Longview, Tex.

[73] Assignee: Witco Corporation, Greenwich, Conn.

[21] Appl. No.: 09/321,287

[22] Filed: May 27, 1999

[51] Int. Cl.$^7$ .................................................. C07C 409/00
[52] U.S. Cl. ........................... 568/564; 568/558; 568/568
[58] Field of Search ..................................... 568/558, 561, 568/564, 568

[56] References Cited

U.S. PATENT DOCUMENTS

| | | |
|---|---|---|
| 2,630,456 | 7/1953 | Bell . |
| 3,047,406 | 7/1962 | Ferrari . |
| 3,151,170 | 9/1964 | Davis . |
| 3,160,677 | 12/1964 | Higashiuchi . |
| 3,288,861 | 11/1966 | Higashiuchi . |
| 3,787,503 | 1/1974 | Cubbon . |
| 4,052,464 | 10/1977 | Priddy . |
| 4,233,462 | 11/1980 | Cubbon ................................... 268/564 |
| 5,288,919 | 2/1994 | Farai . |
| 5,488,176 | 1/1996 | Faraj . |
| 5,488,178 | 1/1996 | Knifton . |

FOREIGN PATENT DOCUMENTS 4438147   5/1996   European Pat. Off. .

OTHER PUBLICATIONS

CA:117:153139 abs of Huaxue Yu Nianhe by Jiao (4) pp. 227–229, 1991.

*Primary Examiner*—Gary Geist
*Assistant Examiner*—Jean F Vollano
*Attorney, Agent, or Firm*—Cook, Alex, McFarron, Manzo, Cummings & Mehler, Ltd.

[57] ABSTRACT

The process of preparing geminal dihydroperoxy alkyl peroxides and 1,1-dihydroperoxydialkyl peroxides, which comprises reacting an aqueous composition comprising a ketone with hydrogen peroxide in the presence of a heteropolyacid.

5 Claims, No Drawings

HETEROPOLYACIDS AS CATALYSTS FOR A SYNTHESIS OF KETONE PEROXIDES

This invention relates to a process of forming geminal dihydroperoxy alkyl peroxides and 1,1-dihydroperoxydialkyl peroxides by a process comprising reacting an alkanone with hydrogen peroxide in the presence of a heteropolyacid.

Geminal dihydroperoxy alkyl peroxides and 1,1-dihydroperoxydialkyl peroxides are generally prepared by reacting an alkanone such as methyl ethyl ketone, with hydrogen peroxide in the presence of a sulfuric acid catalyst. The reaction forming the product can be represented as follows:

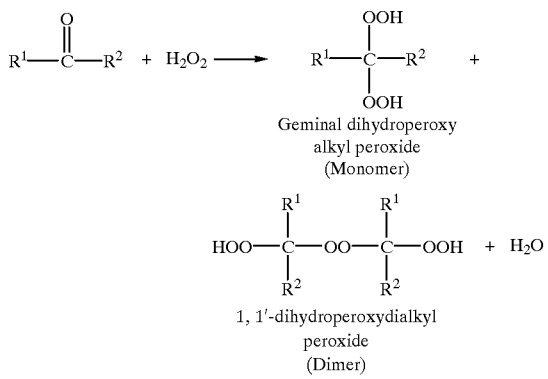

Geminal dihydroperoxy alkyl peroxide (Monomer)

1, 1'-dihydroperoxydialkyl peroxide (Dimer)

In addition to the monomer and dimer, other oligomeric derivatives can be formed, e.g. linear and cyclic trimer.

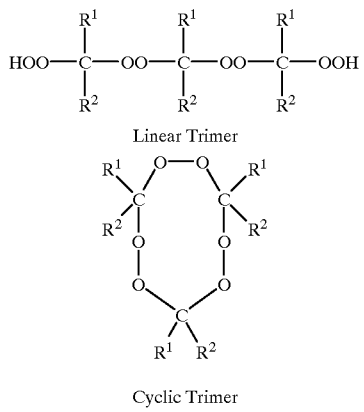

Linear Trimer

Cyclic Trimer

By varying the ratio of the different oligomers, the peroxide product produced can provide a formulation that offers optimum cure performance in a variety of resin types. Synthesis of ketone peroxides is usually carried out in a safety diluent due to the extremely hazardous nature of peroxides derived from low molecular weight ketones and the high exotherm of the process. Methyl ethyl ketone peroxide is the initiator of choices for low temperature (including room temperature) polymerization of alpha, beta-ethylenically unsaturated polyester and styrene.

As pointed out in Faraj U.S. Pat. No. 5,288,919 catalysts such as sulfuric acid, sulfonic acid resins and the like have been used to catalyze the synthesis of dialkyl peroxides from an alcohol such as tertiary butyl alcohol or from a hydroperoxide such as tertiary butyl hydroperoxide. In column 1, lines 24 to 32, Faraj points out that these catalysts have disadvantages including the corrosion and safety hazards associated with the use of sulfuric acid, catalyst deactivation and deterioration associated with the use of catalyst resins, which necessitate the use of azeotropic water removal. Faraj indicates that heteropoly acids can advantageously be used in place of the named acids at 20° C. to 150° C., preferably 40° C. to 110° C. Unfortunately, the process produces relatively low yield of the desired dialkyl peroxides.

Faraj U.S. Pat. No. 5,488,176 is similar to Faraj U.S. Pat. No. 5,288,919 except that it reacts alcohol and/or olefin with hydrogen peroxide at 70–110° C.

Copending U.S. patent application Ser. No. 08/905,593 discloses that the treatment of organic peroxides, including methyl ethyl ketone peroxide, with heteropolyacids is effective in reducing the decomposition temperature of the peroxides to facilitate initiation of certain chemical reactions, such as free-radical polymerization. For example, Table 2 demonstrates that the methyl ethyl ketone peroxide (Hi-Point 90) decomposition temperature is reduced by about 40° C. from around 110° C. to about 70° C.

While it would be desirable to prepare ketone peroxides using a heteropolyacid, heteropolyacids are much more expensive than sulfuric acid; heteropolyacids provide relatively poor yields in the Faraj references and U.S. Patent application Ser. No. 08/905,593 teaches that heteropolyacids reduce the decomposition temperature of ketone peroxides, such as methyl ethyl ketone peroxide.

The general object of this invention is to provide effective, less corrosive and safer catalysts for the preparation of ketone peroxides by the reaction of ketones, particularly methyl ethyl ketone, with hydrogen peroxide. Other objects appear herein after.

It has been discovered that the objects of this invention can be attained by a process comprising the reaction of a ketone, preferably methyl ethyl ketone with hydrogen peroxide in the presence of a heteropolyacid, preferably followed by recovering water insoluble ketone peroxide by separating the aqueous phase (water is a side product of this reaction) containing heteropolyacid from water-insoluble ketone peroxide. While the heteropolyacid in the aqueous phase is effective in catalyzing the desired reaction, the essentially water-insoluble dialkyl ketone peroxides are not decomposed by the heteropolyacid below 80° C. and the ketone peroxides can usually be separated from the aqueous phase.

Suitable ketones contain from about 3 to 13 carbon atoms such as acetone, methyl ethyl ketone, dihexyl ketone, dicyclohexyl ketone, etc.

The molar ratio of hydrogen peroxide to ketone can range from about 1:10 to 10:1, preferably 3:1 to 1:2.

Heteropoly acids generally useful in the present invention are water soluble and have pKa values that are similar in strength to mineral acids.

Of the heteropoly acids useful in the practice of the present invention, those having the formula:

$H_x[X\ M_{12}O_{40}]$ where X is phosphorous or silicon, M is molybdenum or tungsten and x is 3 to 4 are preferred. Examples of heteropoly acids in this regard include, without limitation: phosphotungstic acid ($H_3PW_{12}O_{40}$ or PTA); phosphomolybdic acid ($H_3PMo_{12}O_{40}$); silicotungstic acid ($H_4SiW_{12}O_{40}$); and silicomolybdic acid ($H_4SiMo_{12}O_{40}$).

The heteropolyacid is a non-oxidizing solid reagent which can be easily dissolved in aqueous hydrogen peroxide or water in the reaction medium.

The process can be carried out in the presence of a safety diluent, usually a saturated ester, such as a dialkyl ester of phthalic acid, phosphoric acid, etc. Suitable esters include dimethyl phthalate, trimethyl phosphate, diisopropyl phthalate, etc.

Usually, the reactants are mixed at about −10° to 50° C. After the reaction is complete the aqueous phase containing heteropolyacid is partitioned from the water-insoluble peroxide. If desired, the aqueous phase containing unreacted hydrogen peroxide and heteropolyacid can be recycled for reaction with additional amount of a ketone to form more of the ketone peroxide.

EXAMPLES

Methyl ethyl ketone peroxide was prepared by the addition of methyl ethyl ketone (65.41 g, 0.9072 moles) to a safety diluent, dimethylphthalate (33.70 g, 0.1736 moles) in a 500 mL three neck round bottom flask equipped with a thermometer and a mechanical stirrer. The solution was cooled with a dry ice/acetone bath to 10° C. and then 59.28% wt. aqueous hydrogen peroxide (76.60 g, 1.335 moles) was added while maintaining a reaction temperature of 15° C. At this point, the acid catalyst [e.g. PTA (0.7776 g, 2.700×10$^{-4}$ moles)] was added, and the reaction mixture was maintained at 38° C.±1 for 30 minutes with the aid of a hot water bath. At the end of the cook time, the reaction was terminated by cooling to 15° C. The aqueous and organic phases were separated. The product phase was weighed and analyzed for active oxygen content by iodometric titration. That value was corrected for the amount of free hydrogen peroxide determined by an HPLC method. The ketone peroxide yield was calculated based on the amount of the corrected active oxygen DN content in the product vs. the active oxygen content in the initial amount of hydrogen peroxide. The process was re-run varying the concentration of catalyst. The results are set forth in Table I below.

TABLE I

| Example No. | Molar ratio of PTA to Methyl Ethyl Ketone | % Peroxide Yield |
| --- | --- | --- |
| 1 | 2.976 × 10$^{-4}$ | 68.59 |
| 2 | 5.952 × 10$^{-4}$ | 58.59 |
| 3 | 1.5129 × 10$^{-4}$ | 79.91 |
| 4 | 1.0992 × 10$^{-4}$ | 81.60 |
| 5 | .76964 × 10$^{-4}$ | 78.28 |

Note: For all examples, molar ratio of $H_2O_2$:MEK equalled 1.47.

We claim:

1. The process of preparing geminal dihydroperoxy alkyl peroxides and 1,1-dihydroperoxydialkyl peroxides, which comprises reacting an aqueous composition comprising a ketone with hydrogen peroxide in the presence of a heteropolyacid.

2. The process of claim 1 wherein the ketone comprises methyl ethyl ketone.

3. The process of claim 1 wherein the heteropolyacid is phosphotungstic acid.

4. The process of preparing geminal dihydroperoxy alkyl peroxides and 1,1-dihydroperoxydialkyl peroxides, which comprises (1) reacting a composition comprising a ketone and hydrogen peroxide in the presence of a heteropolyacid and (2) separating the water-insoluble peroxide from the aqueous phase containing heteropolyacid.

5. The process of claim 3, wherein the ketone comprises methyl ethyl ketone.

* * * * *